United States Patent
Nekoksa

[11] Patent Number: 6,060,877
[45] Date of Patent: May 9, 2000

[54] FLAT CATHODIC PROTECTION TEST PROBE

[76] Inventor: George Nekoksa, 209 Gaucho Ct., San Ramon, Calif. 94583

[21] Appl. No.: 09/033,108

[22] Filed: Mar. 2, 1998

Related U.S. Application Data

[60] Provisional application No. 60/040,619, Mar. 5, 1997.

[51] Int. Cl.⁷ .................................................. G01N 27/42
[52] U.S. Cl. ..................................... 324/71.1; 204/196.06
[58] Field of Search ................................... 324/450, 425, 324/72.5, 71.1; 204/196.06, 196.07, 197

[56] References Cited

U.S. PATENT DOCUMENTS

| | | | |
|---|---|---|---|
| 2,943,028 | 6/1960 | Thayer et al. | 204/409 |
| 4,065,373 | 12/1977 | Martin et al. | 204/195 |
| 4,080,565 | 3/1978 | Polak | 324/71 R |
| 4,351,703 | 9/1982 | Winslow | 204/1 T |
| 4,409,080 | 10/1983 | Slough | 204/196 |
| 4,414,511 | 11/1983 | Waits et al. | 324/347 |
| 4,489,277 | 12/1984 | Goolsby | 324/425 |
| 4,639,677 | 1/1987 | Goolsby | 324/425 |
| 4,786,388 | 11/1988 | Tatum | 204/197 |
| 5,144,247 | 9/1992 | Speck | 324/425 |
| 5,216,370 | 6/1993 | Bushman | 324/425 |
| 5,469,048 | 11/1995 | Donohue | 324/71.1 |
| 5,712,559 | 1/1998 | Moore et al. | 324/71.1 |

OTHER PUBLICATIONS

Metals Handbook, 9th Ed., V. 13, Corrosion, ASM International, Metals Park, Ohio, 1987, pp. 466–477. No month available.

Stephen P. Turnipseed and George Nekoksa, "Potential Measurment on Cathodically Protected . . . ", NACE Int., MP, Jun. 1996, pp. 21–25.

George Nekoksa and Stephen P. Turnipseed, "Potential Measurements on Integrated Salt Bridge . . . ", NACE Int., Paper 206, Mar. 25/29–96.

George Nekoksa and Stephen P. Turnipseed, "Laboratory and Field Testing of . . . ", Paper at 13th Int. Corrosion Conference, Melbourne, Australia, Nov. 25–29, 1996.

R.A. Gummow, "Cathodic Protection Potential Criterion . . . ", NACE International, Materials Performance, Nov. 1993, pp. 21–30.

Brian A. Martin, "Cathodic Protection of a Remote River Pipeline", NACE International, Materials Performance, Mar. 1994, pp. 12–17.

Komei Kasaharaet al., "An Improved Method for Measuring Pipe–to–SoilPotential . . . " NACE International, Materials Performance, Mar. 1979, pp. 21–25.

John Mc Coy, "Cathodic Protection on the Dampier to Perth Pipeline.", NACE International, Materials Performance, Feb. 1989, pp. 16–20.

*Primary Examiner*—Diep N. Do
*Assistant Examiner*—Vincent Q. Nguyen
*Attorney, Agent, or Firm*—David Pressman

[57] ABSTRACT

A flat cathodic protection test probe comprises a non-metallic probe body (20) with a mounted metal coupon (18) simulating a large coating holiday on a pipeline, an insulated wire(s) (22) attached to the coupon for an electrical connection to the pipeline, a non-metallic tube (16) filled with a conductive backfill (26), and a narrow and long porous potential sensing strip(s) (40) mounted flush with the coupon exposed surface in the central area of the coupon. The coupon is electrically insulated from the conductive backfill by a non-metallic coating (38) and an epoxy compound for electrical insulation (42). To determine if the pipeline is fully cathodically protected, the flat cathodic protection probe is buried next to the pipeline and interconnected by the insulated wire(s) with the pipeline. The potentials taken on the probe will not include a substantial voltage drop in soil and will not be adversely affected by shielding of the coupon by a reference electrode or its access tube to invalidate the reading. To measure the probe potential, a calibrated reference electrode (24) is lowered into the tube to make an electrical contact with the conductive backfill and a high impedance voltmeter (36) is connected to the coupon and to the reference electrode. No interruption of the cathodic protection to the pipeline or coupon is necessary.

17 Claims, 3 Drawing Sheets

FLAT CATHODIC PROTECTION TEST PROBE

BACKGROUND—CROSS REFERENCES TO RELATED APPLICATIONS

This application is entitled to the benefit of provisional patent application, No. 60/040,619, filed Mar. 5, 1997. Existing cathodic protection probes with cylindrical coupons have been described in patent applications Ser. No. 08/028,484, filed Mar. 8, 1993 and Ser. No. 08/276,011, filed Jul. 15, 1994 of Stephen P. Turnipseed and George Nekoksa, now abandoned.

BACKGROUND—PRIOR ART

This invention relates to testing and evaluating cathodic protection effectiveness on buried or submerged metallic structures, specifically to the evaluation of corrosion protection levels on coated pipelines, tanks, piles, and piping systems.

Buried or submerged metallic structures, such as pipelines, tanks, and distribution piping systems are usually coated with non-conductive material to prevent corrosion. If any corrosion occurs in any uncoated areas of the structure many adverse affects will occur, such as loss of transported product, possible fires and explosions caused by leaking gas and fuel oil, and contamination of the environment. To prevent these effects, most pipelines are provided with corrosion protection consisting of cathodic protection, in addition to the non-conductive coating.

Cathodic protection provides corrosion protection to any bare metal areas exposed to soil due to coating defects or "holidays" by causing direct current to flow from the soil into the structure, thereby polarizing the structure as a cathode. The required direct current output of the cathodic protection system is reduced to manageable levels by the coating, which substantially reduces the bare metal area of the structure exposed to soil.

Two cathodic protection systems are in use for corrosion protection of metal structures. The first, termed an impressed current cathodic protection system, consists of a rectifier, insulated wires connecting the plus terminal of the rectifier to a buried anode (for instance graphite cylinders), insulated wire connecting the negative terminal of the rectifier to the protected structure, and test stations installed at the structure. The test stations typically consist of a pipe or a valve box with one or two insulated wires attached to the structure, typically by brazing, and a terminal board for termination of the wires. The test stations are used for monitoring the corrosion protection levels by measuring potentials between the structure and a reference electrode in an electrical contact with ground above the structure. The reference electrode usually consists of a copper rod fixed in a plastic body filled with saturated copper-sulfate solution, and having a porous plug to facilitate electrical contact with the ground.

The second, termed a sacrificial (galvanic) cathodic protection system, consists of magnesium, zinc or aluminum anodes buried next to the structure and often directly connected by an insulated wire to the structure. The protective current is generated by the potential difference between the structure and the anode. The structure with sacrificial anodes also has test stations for the cathodic protection testing and evaluation of its corrosion protection effectiveness.

Details of different cathodic protection systems and of the pipeline potential measurements can be found in Metals Handbook, Volume 13, Corrosion, published by ASM International, Metals Park, Ohio, 1987.

The objective of the cathodic protection is to shift the potential of the structure in a negative direction. The potential shift must be large enough to mitigate structure corrosion. Potential criteria have been developed by the National Association of Corrosion Engineers (RP0169-92) to provide guidance for determination of safe cathodic protection levels to mitigate corrosion. One of the criteria is based on a single value of potential, measured with a regular high-impedance voltmeter with the cathodic protection system operating. The potentials measured with the cathodic protection operating are identified as "on" potential readings. This criterion is very easy to make. However it requires a consideration or elimination of voltage drops in soil between the reference electrode and the structure. Another criterion is based on achieving the same value of structure potential immediately after interrupting the cathodic protection system, and is identified as an "off" potential reading. Another criterion is based on a single value of the structure potential decay, measured from the "off" potential, leaving the cathodic protection system disconnected for several hours or days.

There is no easy and practical method to determine the soil-voltage drop when the "on" potential reading is taken. Therefore, the "off" potential readings, which eliminate the soil voltage drop measured immediately after interrupting the cathodic protection system from the structure, are often used for monitoring corrosion protection levels. However, the "off" potential readings are much more difficult to take than the "on" readings. The interpretation of the "off" potential readings is also much more complex. The "off" potential readings often require use of synchronized current interrupters, fast reacting recorders, oscilloscopes, or wave analyzers. The "off" potential readings after cathodic protection is interrupted can be adversely affected by long-cell currents in the pipeline caused by currents flowing between the more polarized structure sections in the proximity of the rectifiers and less polarized sections, typically in the middle between the rectifiers. Also, the "off" potential readings are often adversely affected by inductive or capacitive voltage spikes, caused by cathodic protection interruption. If the "off" potential reading is taken some time after the spike, some of the polarization is lost and the reading could be therefore invalid.

Meeting the "off" potential criterion often requires that more cathodic protection current be applied than the "on" potential criterion, resulting in possible overprotecting the structure, faster deterioration of the coating, and a higher probability of hydrogen evolution and structure steel embrittlement. The "off" potential measurements are not valid in areas where substantial uninterruptable direct currents are flowing through the soil into or from the structure, polarizing the structure. Such conditions exist, for instance in stray current areas, where the structure is affected by stray currents from electric railroads, from cathodic protection systems on foreign structures, and in areas with telluric (earth) currents naturally induced by fluctuations in the earth's magnetic field. Also, the "off" potential readings cannot be used on structures with distributed galvanic anodes directly connected to the structure.

To eliminate some of the disadvantages of the "off" potential readings on the structure, different cathodic protection test probes and coupon/access tube assemblies have been proposed. A coupon is a metal electrode which simulates a coating holiday on the structure. Coupons are made from the same or similar metal as the structure, and are electrically connected to the structure to receive cathodic protection. The main disadvantages of such prior-art systems can be best demonstrated on cathodically protected and coated pipelines.

Cathodic protection probes with cylindrical coupons, now commercially available, have been described in the above abandoned patent applications and in Material Performance, published by National Association of Corrosion Engineers, Houston, Tex., June 1996, pp. 21–24. The probes consist of a short steel pipe section as a coupon, a plastic tube filled with conductive backfill functioning as an electrolytic "salt bridge", and a porous ceramic plug glued to the end of the plastic tube, representing a potential sensing area. The coupon of the probe simulates a coating holiday on the pipeline. The coupon is electrically connected with insulated wires to the pipeline in a test station and therefore it receives cathodic protection. Cathodic protection probes with cylindrical coupons are easy to manufacture and install. However, they receive the protective current from all sides while the coated pipeline limits the space for the current flow into the coating holiday. The electric field in soil at the cylindrical coupon is therefore different than at the coating holiday. Because the cylindrical coupon receives more current per square area than the coating holiday, the protection level on the coupon could be higher than in the coating holiday.

Measurements of the "on" and "off" potentials in stray current areas and in electric fields around the protected pipelines without any substantial voltage drop in soil require that the distance between the potential sensing area, represented by a porous material surface in contact with soil, and the coupon be very small. This is difficult to accomplish on a probe with a cylindrical coupon because the distance between the center of the sensing area and the coupon is given by the diameter of the pipe section (coupon) and by an application of a heat-shrink tubing over the lower part of the coupon. The heat-shrink tubing is necessary because it eliminates the effect of higher corrosion protection levels at the end of the pipe section close to the sensing area. A very small sensing area in the side of the pipe section substantially decreases the distance between the center of the sensing area and the coupon. However, it provides a small, poor, and unreliable electric contact with soil.

Several different proposals have been made to eliminate the voltage drops in soil when measuring the pipeline potentials against a reference electrode. For instance, U.S. Pat. No. 4,080,565 (1978) to Josef Polak at al., U.S. Pat. No. 4,351,703 (1982) to Joseph D. Winslow, U.S. Pat. No. 4,409,080 (1983) to Carlton M. Slough, U.S. Pat. No. 4,489,277 (1984) and U.S. Pat. No. 4,639,677 (1987) both to Alvin D. Goolsby, U.S. Pat. No. 5,144,247 (1992) to Robert M. Speck, U.S. Pat. No. 5,216,370 (1993) to James B. Bushman, and U.S. Pat. No. 5,469,048 (1995) to Charles W. Donohue propose using coupons or other methods to eliminate the voltage drop in soil for cathodic protection testing.

The Polak et al. patent shows a probe comprising a reference electrode, permanently imbedded inside the probe, and several coupons. This probe suffers from the following disadvantages:

a. The potential readings on the coupons must be taken as "off" readings. The "off" readings should be taken immediately after disconnecting the coupon from the pipeline to eliminate coupon potential decay. This often requires use of fast recorders powered by a battery instead of regular high impedance voltmeters. The "off" potential testing is also more complex and time consuming than the "on" testing with regular voltmeters when no coupon disconnection is required.

b. The probe does not eliminate soil voltage drops from the "off" readings in areas with stray currents which often cannot be interrupted.

c. The semi-permanent reference electrode is built into the probe. This reference electrode cannot be calibrated or monitored for contamination and cannot be replaced without digging out the probe.

Winslow, Jr. recommends installing metallic specimens adjacent to structure. This method could be useful for corrosion rate measurement and determination of cathodic protection current density, but it is not useful for determination of the potentials indicating the level of cathodic protection on the pipeline.

Slough proposes to install a coulomb meter (charge measurer) between the buried structure and a buried small target electrode. This system monitors current flow that relates to a buried structure which is under cathodic protection. It cannot be used to monitor pipeline or coupon potentials to determine the cathodic protection levels.

The Goolsby patents recommend installation of a semi-permanent reference electrode (half cell) on a submerged platform at the metallic plate of a monitoring section. Monitoring for contamination and calibration of the semi-permanent reference electrode is time consuming and costly. It can be done only by use of divers. No means are provided to monitor the stability of the reference electrode to ensure that the potential readings are correct.

The Speck patent describes a cathodic protection monitoring probe having a reference electrode, working and auxiliary electrodes. An electrical contact with ground is provided through a porous ceramic plug at the end of the probe. The recommended method and apparatus suffers from the following disadvantages:

a. Testing requires complex circuitry and complicated procedures and interpretation.

b. The probe is not permanently buried in soil. To stabilize the working electrode potential requires time, usually hours. This makes the testing time consuming and costly.

Bushman describes a cathodic protection monitoring system which measures the polarized potential between a reference electrode and a coupon subsequent to decoupling the coupon from the protected structure ("off" potential reading). To eliminate inductive or capacitive voltage spikes caused by the decoupling, Bushman suggests using a complex circuit to determine the potential reading only after the potential has achieved a relatively steady state value.

Donohue, in his preferred embodiment (FIG. 2) shows a cathodic protection measurement apparatus comprising a coupon fixed to the access tube of the test station, an electrode access tube for the reference electrode, electric switch to take "off" potential coupon potential readings, and necessary wiring. Donohue claims that his apparatus will substantially remove any voltage drop in soil if the reference electrode is sufficiently close (one inch) to the coupon. Donohue's system has the following problems and disadvantages:

a. The space between the coupon, test station access tube, reference electrode access tube and pipeline is very small and will result in shielding the coupon from the cathodic protection current. This is especially so if the distance between the coupon and the reference electrode access tube were one inch (claim 9), I.e., the top of the coupon sensed by the reference electrode would be substantially shielded from the protective current flowing from the soil into the coupon and the coupon potential will be lower than a similar coating holiday on the pipeline.

b. FIG. 3 shows that the apparatus performs poorly when monitoring the "on" coupon potential readings. The coupon "on" potential with the reference electrode at the earth surface was 1140 mV, the coupon "on" potential with the reference electrode in the reference electrode access tube at the coupon was 1123 mV, and the coupon "off" potential was 950 mV. This indicates that the apparatus eliminated, from the total voltage drop in soil of 190 mV (1140–950 mV), only 17 mV (1140–1123 mV). The effectiveness of this apparatus in eliminating the voltage drop in soil when the "on" potential readings were taken with the reference electrode in the access tube was therefore only 8.9 percent.

c. The distance between the coupon and the reference electrode access tube is not fixed. During installation and after soil settlement, this distance could increase or decrease and change the performance of the apparatus. Also, because the reference electrode access tube is not filled with a conductive backfill, the diffusion rate of oxygen to the top of the coupon will be much higher than to the protected pipeline, resulting in different potentials on the coupon and on the pipeline.

OBJECTS AND ADVANTAGES

Accordingly several objects and advantages of the present invention are:

a. to provide an improved, more reliable, and easier-to-use cathodic protection probe;

b. to provide cathodic protection test probe which can be used optionally for the "off" potential readings, but preferably for the more easy-to-do and simple to interpret "on" potential readings without invalidating the readings with any substantial voltage drops in soil;

c. to provide a cathodic protection test probe which represents more closely a typical large coating holiday on the pipeline than other geometries;

d. to provide a cathodic protection test probe with large exposed area of the porous sensing strip to ensure permanent and low resistance contact with soil;

e. to provide a cathodic protection test probe where the coupon is not shielded from the protection current flow by a reference electrode or by access tubes to ensure that the coupon will properly represent a coating holiday of similar size and geometry;

f. to provide a cathodic protection test probe in which the pipeline does not shield the coupon or part of the coupon from the protection current flow;

g. to provide a cathodic protection test probe in which a permanent and low resistance contact with soil is ensured;

h. to provide a cathodic protection test probe in which the distance between the coupon and the porous sensing area is permanently fixed and will not be affected by soil settlement.

i. to provide a cathodic protection test probe in which the reading on the probe represents the least protected area of the coupon; and j. to provide a cathodic protection test probe which can be manufactured and assembled in a factory, thus ensuring high quality of the product.

Further objects and advantages are to provide a cathodic protection test probe which can be simple to manufacture and install. Yet further objects and advantages will become apparent from a consideration of the following description and accompanying drawings.

DRAWING FIGURES

REFERENCE NUMERALS IN DRAWINGS

| | |
|---|---|
| 12 | pipeline |
| 14 | flat cathodic protection test probe |
| 16 | non-metallic tube |
| 18 | metal coupon |
| 20 | non-metallic probe body |
| 22 | insulated wire(s) |
| 24 | reference electrode |
| 26 | conductive backfill |
| 28 | test station |
| 30 | terminal board |
| 32 | bar or switch |
| 34 | voltmeter test leads |
| 36 | high impedance voltmeter |
| 38 | non-metallic coating |
| 40 | porous strips |
| 42 | electrical insulation |
| 44 | brazed connection |

SUMMARY

In accordance with the present invention a flat cathodic protection test probe comprises a metallic probe body having a metal coupon simulating a large coating holiday on a pipeline, insulated wire(s) attached to the coupon for an electrical connection to the pipeline, a non-metallic tube filled with a conductive backfill, and narrow and long porous potential sensing strips mounted flush with the coupon exposed surface in the central area of the coupon. The coupon is electrically insulated from the conductive backfill by an epoxy coating and epoxy compound.

To determine if the pipeline is fully cathodically protected, the flat cathodic protection probe is buried next to the pipeline, the non-metallic tube is extended above the surface of the ground, and the probe is interconnected by the insulated wire(s) with the pipeline. The potentials taken on the probe will not include any substantial soil voltage drop and will not be adversely affected by shielding of the coupon by a reference electrode or its access tube to invalidate the reading. To measure the probe potential, a calibrated reference electrode is lowered into the tube to make electrical contact with the conductive backfill and a high impedance voltmeter is connected to the coupon and to the reference electrode. No interruption of the cathodic protection to the pipeline or coupon is necessary.

Figure 1:
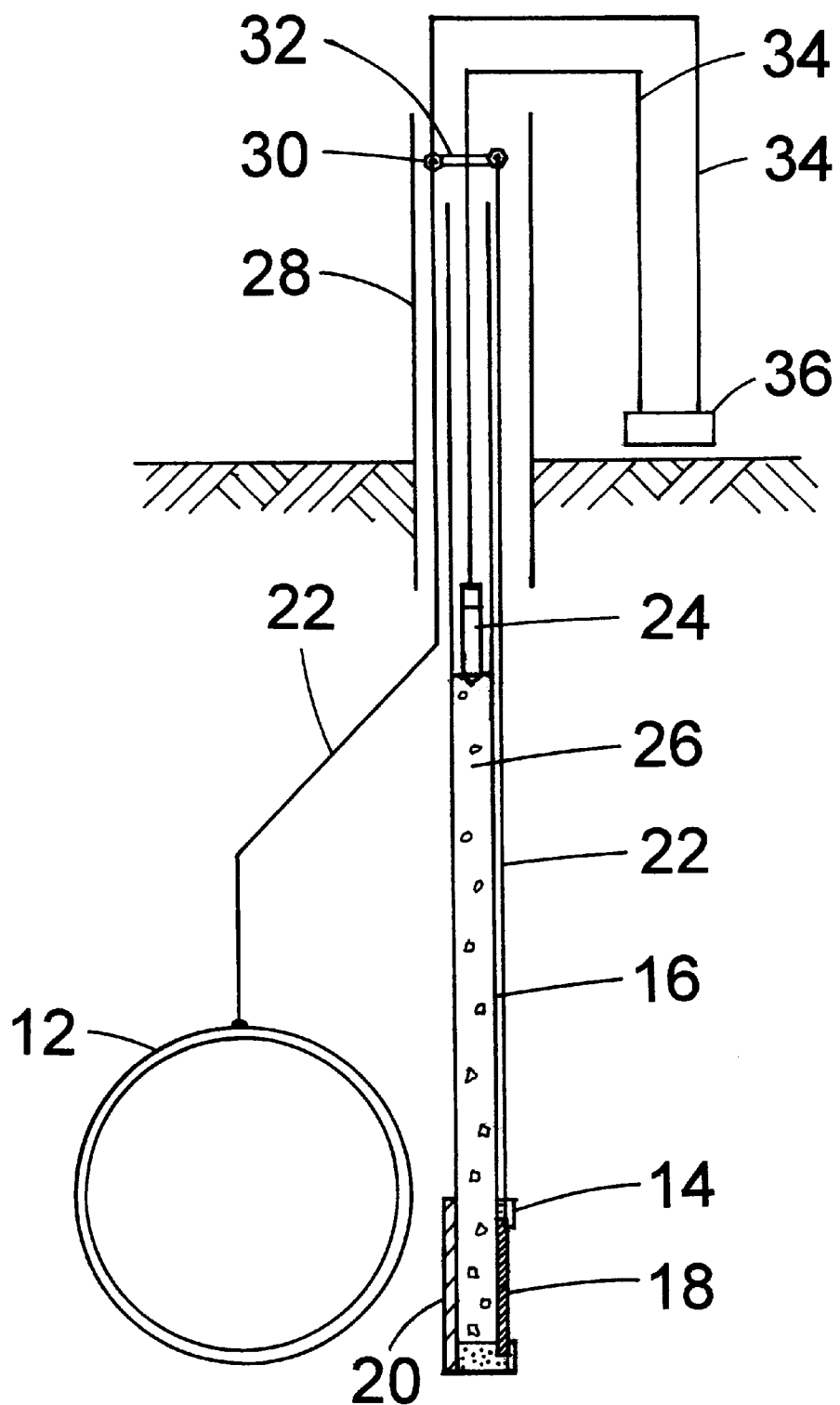
FIG. 1 shows a cross section of a pipeline and a flat cathodic protection test probe installed in a test station in accordance with the invention.
Figure 2A:
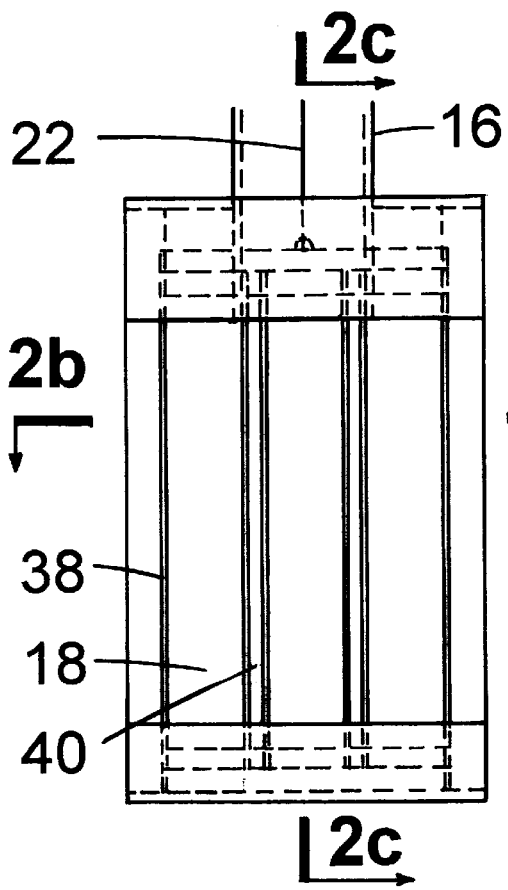
FIG. 2a shows a frontal view of the probe with a boxy probe body.
Figure 2C:
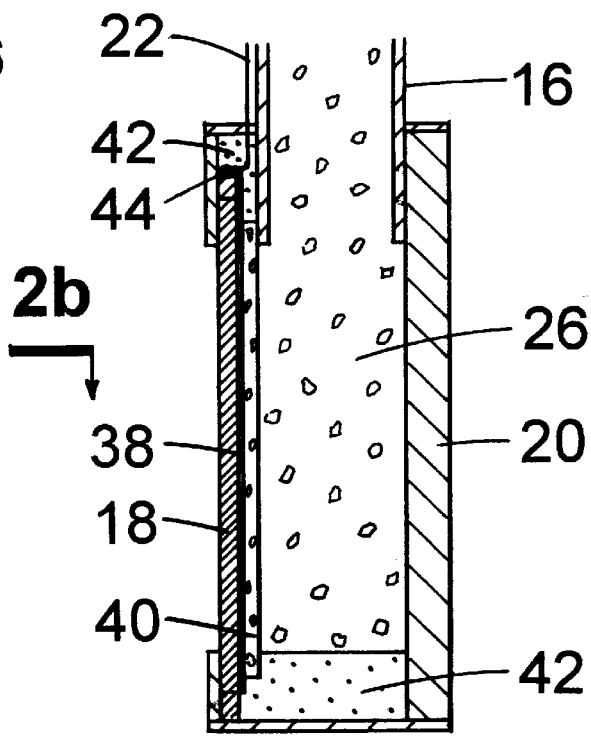
FIGS. 2b and 2c show a vertical and horizontal cross sections of the probe.
Figure 2B:
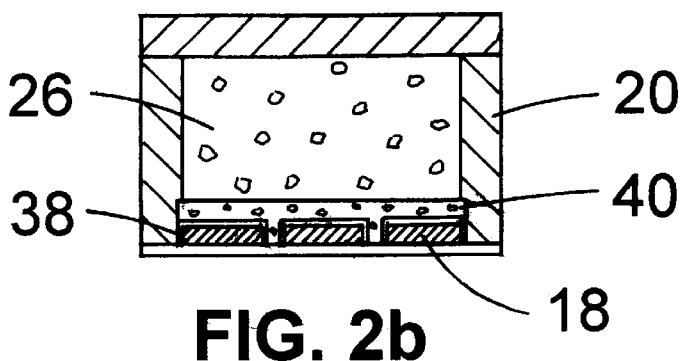
Figure 3:
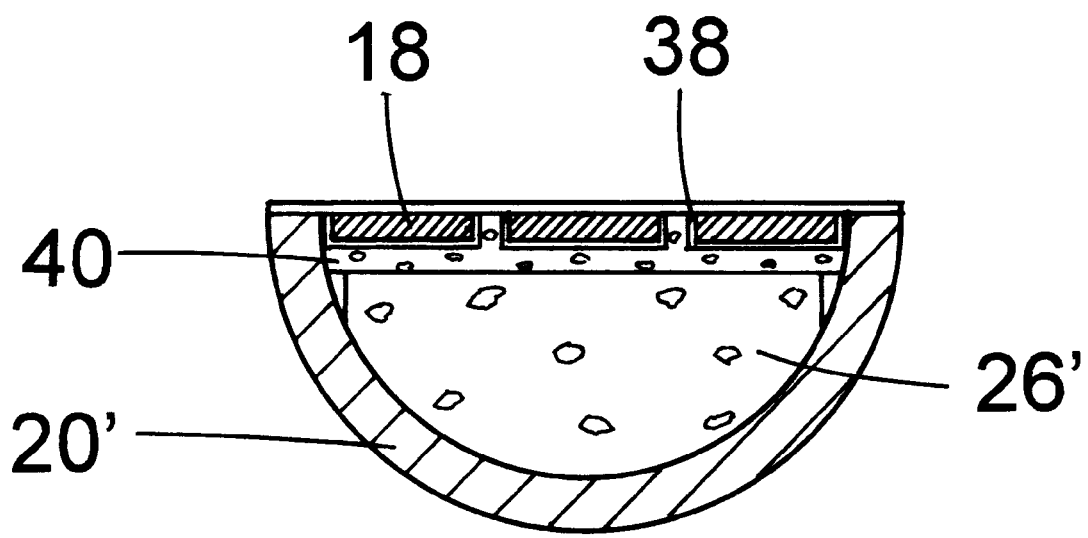
FIG. 3 shows a cross section of an alternative probe with a half-cylindrical probe body, in accordance with the invention.

Descriptioin—FIGS. 1 to 3

A typical embodiment of a flat cathodic protection test probe ("probe") of the present invention is illustrated in FIG. 1 (cross section of a pipeline and an installed probe), FIG. 2a (front view of the probe), FIG. 2b (horizontal cross-section of the probe), and FIG. 2c (vertical cross-section of the probe). As shown in FIGS. 2a, 2b, 2c, the probe 14 consists of a non-metallic probe body 20, a non-metallic tube 16, porous strips 40, and a metal coupon 18 electrically isolated from a conductive backfill 26 and from the porous strips 40 by a non-metallic coating 38 and an electrically insulating layer 42. As shown in FIG. 1, coupon 18 is electrically interconnected with a pipeline 12 by insulated wire(s) 22 on a terminal board 30 in a test station 28 through an optional bar or a switch 32. The potential measurement is taken with a high impedance voltmeter 36 (preferably at least 10 million ohm), voltmeter test leads 34, and a portable reference electrode 24.

In the preferred embodiment, non-metallic tube 16 and non-metallic probe body 20 are made from PVC (polyvinyl chloride) or any other non-metallic material which can be easily glued, welded, or extruded. Tube 16 must be easily coupled and cut in the field to extend the tube into test station 28. Coupon 18 is of the same or similar composition as pipeline 12, e.g., steel. The back and sides of coupon 18 are electrically isolated from porous strips 40 and conductive backfill 26 in probe body 20 by non-metallic coating 38 applied as several epoxy coats. Insulation 42 is preferably an epoxy compound; it fixes coupon 18 and porous strips 40 in probe body 20 and also insulates coupon 18 from conductive backfill 26 and porous strips 40. Strips 40 are mounted flush with the exposed coupon surface and are located in the central area and away from the outside edges of coupon 18. Strips 40 are between 1 mm and 10 mm wide and are made from porous ceramic or a porous material prepared from a mixture of fine aggregate with a bonding agent, e.g., epoxy. Backfill 26 is prepared from water and conductive soil or from water and a mixture of bentonite and sand. Preferably, two insulated copper wires 22 are brazed to coupon 18 and the brazed connection 44 is sealed by insulation 42 provided by the epoxy compound.

An alternative embodiment is shown in FIG. 3. There are various possibilities with regard to the geometries of the coupon, porous strips, and the body of the probe. FIG. 3 represents a probe with a coupon 18 and a non-metallic probe body 20' made from half of a plastic or fiberglass pipe. Coupon 18 is insulated from a conductive backfill 26' and strips 40 by coating 38.

Advantages

From the description above, a number of advantages of my flat cathodic protection test probe become evident:

a. The cathodic protection test probe uses porous potential sensing strips installed flush with the coupon. The porous strips present no obstruction to the current flow into the coupon or coupon shielding. (Cf. the prior-art use of a reference electrode and an access tube, which decrease the current density and protection levels on the coupon, making the readings invalid.)

b. The probe with long but narrow porous potential sensing strips can be used for more simple and easy-to-interpret "on" potential readings without invalidating the readings with any substantial voltage drops in soil. So, for instance, when a probe with two 3.2 mm wide porous strips was tested in a laboratory in a 225-liter tank filled with potable water, it eliminated between 96 and 98 percent of the voltage drop in water. The effectiveness of the probe was calculated from the "on" potential with the reference electrode at the water level, "on" potential with the reference electrode in the non-metallic tube, "on" potential with the reference electrode with a capillary tip at the coupon/water interface, and "off" potential with the reference electrode in the tube.

c. The probe provides a large exposed area of the porous strips to ensure permanent and low resistance contact with soil. A large contact area between the porous strips and soil is very important in high resistivity soils with low moisture content, such as soils with rocks, gravel, and sand. A large contact area between the porous strips and soil is especially important in regions with long and dry seasons.

d. The probe with a flat coupon exposed on only one side better represents a typical large coating holiday on a pipeline much better than other geometries, such as pipe sections, cylinders, bare plates with both sides exposed, and especially rods. A flat coupon exposed only on one side will receive similar current density and protection level as a coating holiday of similar area and geometry on the pipeline.

e. The probe eliminates a substantial part of the voltage drop in soil and can be used for simple "on" potential measurements, even in areas with stray currents, in congested pipeline corridors with many cathodic protection systems, and on distribution systems where it is difficult to achieve electric contact between the reference electrode and the soil above the pipeline because of large paved areas.

f. The probe can be also used for optional "off" potential readings, not only in areas without stray currents, but also in areas with stray and telluric currents, and in pipeline corridors with many interacting cathodic protection systems without including any substantial voltage drops.

Operation—FIGS. 1, 2a, 2b, 2c

The manner of using the probe is similar to those in present use. Namely, the non-metallic tube of the probe is extended by gluing or coupling to reach above the ground surface. Then the probe is installed next to the pipeline, so that it is exposed to the same soil as the pipeline. Because coupon 18 is exposed only on one side, as is shown in FIG. 1, it must face away from pipeline 12 to allow unshielded access by the protection current into coupon 18. The body of probe 20 and non-metallic tube 16 are filled with a mixture of water and conductive soil or a mixture of water, bentonite, and sand. A test station 28 is installed over the or next to tube 16 and insulated wires 22, attached to the coupon, are connected on terminal board 30 and through an optional bar or switch 32 to pipeline 12. The potential testing on the probe requires a portable reference electrode 24 to be lowered into tube 16. The potential reading is taken with a high impedance voltmeter 36 and test leads 34. One terminal of voltmeter 36 is connected to the reference electrode 24 and its second terminal is connected to wires 22 on terminal board 30.

The simple-to-do "on" potential tests, as well as the optional and more complex and time consuming "off" potential tests, and also the potential decay tests can be made without any substantial error caused by the voltage drop in soil—even in areas with strong stray and telluric currents. The probe can also be used to measure electric current between the pipeline and the coupon by inserting a shunt between the pipeline and coupon wires and measuring the voltage drop on the shunt. If the probe is left disconnected from the pipeline, the resistivity and corrosivity of soil, using a linear polarization method, and the corrosion potential of the coupon can be determined.

CONCLUSIONS, RAMIFICATIONS, AND SCOPE

The present probe, therefore, provides a simple, easy to use, inexpensive, and reliable. It can be used to monitor cathodic protection levels on a pipeline and other metallic structures using the "on" potential method, which does not require interruption of the cathodic protection current nor complex test equipment to read the coupon potential immediately after current interruption. A simple high impedance voltmeter and a portable pre-calibrated reference electrode are the only equipment required for the "on" potential reading. As an option, the probe can be also used for measuring the "off" potentials. The advantage of this test probe is that the "off" readings can be also taken in areas with stray currents and in corridors congested with pipelines and with multitude of cathodic protection systems.

Although the description of the invention above contains many specificities, these should not be construed as limiting the scope of the invention but as merely providing illustrations of some of the presently preferred embodiments of this invention. For example, the body of the probe can have other shapes, such as oval, or circular; the porous strips can be replaced by rows of porous circles, squares or rectangles, more than one coupon with an insulated wire can be used in one probe, etc. The terminal board can be eliminated in favor of direct or continuous connections. Also the materials, shapes, and interconnections shown can be varied.

Thus the scope of the invention should be determined by the appended claims and their legal equivalents, rather than by the examples given.

I claim:

1. A flat cathodic protection test probe for monitoring the corrosion protection levels on a buried metallic or submerged structure, comprising:
   a non-metallic probe body;
   a flat metal coupon permanently fixed into said probe body;
   a porous strip permanently fixed into said probe body;
   a non-conductive tube permanently fixed into said probe body;
   an insulated wire attached to said coupon;
   a conductive backfill filling said probe body and said non-conductive tube; and
   a means for insulating said metal coupon from said conductive backfill and said porous strip,
   whereby the cathodic protection levels are measured without any substantial and invalidating voltage drop in soil.

2. The flat cathodic protection test probe of claim 1 wherein said porous strip is less than 15 mm wide to eliminate a substantial part of any voltage drop in soil when said probe body and said porous strip are embedded in soil and connected to a voltage source.

3. The flat cathodic protection test probe of claim 1 wherein said porous strip is at least 20 mm long to provide a low-resistance and permanent electric contact between said porous strip and soil, when said probe body and said porous strip are embedded in soil and connected to a voltage source.

4. The flat cathodic protection test probe of claim 1 wherein said porous strip is located in a central area of said coupon to provide readings with minimum corrosion protection levels.

5. The flat cathodic protection test probe of claim 1, further including a reference electrode embedded into said conductive backfill.

6. The flat cathodic protection test probe of claim 1, further including a plurality of insulated wires attached to said metal coupon.

7. The flat cathodic protection test probe of claim 1, further including a plurality of porous strips permanently fixed into said probe body.

8. A method for measuring the potential of a cathodically protected, buried, or submerged metal structure without any substantial voltage drop in water or soil to determine its corrosion protection level, comprising the steps of:
   installing a flat cathodic protection test probe having a coupon next to a cathodically protected structure so that it receives cathodic protection current;
   extending a non-conductive tube of said flat cathodic protection test probe above the surface of said water or soil;
   filling said non-conductive tube with a conductive backfill;
   installing a test station over said non-conductive tube;
   connecting an insulated wire attached to said coupon of said flat cathodic protection test probe to said cathodically protected structure;
   inserting a reference electrode into said non-conductive tube, so that said electrode is in electrical contact with said conductive backfill;
   connecting one terminal of a high impedance voltmeter to said reference electrode and another terminal to said insulated wire from said coupon and said cathodically protected structure; and
   measuring potential of said coupon with and without an interruption of protective current flow into said coupon,
   whereby said potential is measured without any substantial and invalidating voltage drop in soil.

9. The method of claim 8 wherein said reference electrode is portable, so that it can be calibrated and inserted and removed from said non-conductive tube.

10. The method of claim 8 wherein said reference electrode is stationary and is embedded in said conductive backfill in said non-conductive tube.

11. The method of claim 8, further including means for disconnecting said insulated wire between said metal coupon and cathodically protected structure.

12. The method of claim 11, further comprising interrupting the current flow into said metal coupon by said means for disconnecting said insulated wire between said metal coupon and said structure, thereby providing an option to measure said coupon potential after interruption with no substantial and invalidating voltage drop in soil.

13. The method of claim 8, further including a plurality of insulated wires attached to said coupon, so that the electrical continuity of said wires and the wire and coupon connection can be tested.

14. The method of claim 8, further including a plurality of narrow porous strips fixed into said probe body, so that the contact area between said porous strips and soil is at least 25 sq. mm to ensure low electrical contact resistance to soil.

15. A flat cathodic protection test probe for monitoring the corrosion protection levels on a buried cathodically protected steel pipeline, comprising:
   a plastic probe body having at least one side;
   a flat conductive coupon permanently fixed into said one side of said probe body;
   two porous strips permanently fixed into said probe body;
   an insulating tube permanently fixed into said probe body;
   two insulated wires connected to said metal coupon;
   a conductive backfill filling said probe body and said plastic tube; and
   a coating insulating said metal coupon from said conductive backfill and said porous strips.

16. The probe of claim 15 wherein said conductive backfill contains at least 40 percent clay to lower the resistivity and permeability of said conductive backfill.

17. The probe of claim 15 wherein said flat conductive coupon is made of steel and is fixed to said probe body by an epoxy compound.

* * * * *